(12) United States Patent
Hsu et al.

(10) Patent No.: US 7,195,771 B1
(45) Date of Patent: Mar. 27, 2007

(54) WATER-SOLUBLE LOTIONS FOR PAPER PRODUCTS

(75) Inventors: Jay C. Hsu, Alpharetta, GA (US); Ed Rosenthal, San Antonio, TX (US); Richard L. Shick, Alpharetta, GA (US); Audra S. Wright, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 165 days.

(21) Appl. No.: 09/718,071

(22) Filed: Nov. 21, 2000

(51) Int. Cl.
*A01N 25/34* (2006.01)
*A61K 9/00* (2006.01)
*A61K 13/00* (2006.01)

(52) U.S. Cl. ............... 424/402; 424/400; 424/443
(58) Field of Classification Search .......... 424/401, 424/402, 484, 78.02, 78.03, 400, 443; 514/844, 514/847, 953
See application file for complete search history.

(56) References Cited

U.S. PATENT DOCUMENTS

| | | |
|---|---|---|
| 85,188 A | 12/1868 | Thompson |
| 302,073 A | 7/1884 | Wheeler |
| 1,687,625 A | 10/1928 | Mackenzie |
| 1,687,643 A | 10/1928 | Berliner |
| 1,743,512 A | 1/1930 | Aisen |
| 1,786,513 A | 12/1930 | Zuckerman |
| 1,868,862 A | 7/1932 | Washburn |
| 2,093,824 A | 9/1937 | Woronoff |
| 2,251,328 A | 8/1941 | Ehret |
| 2,390,921 A | 12/1945 | Clark |
| 2,432,091 A | 12/1947 | Englund |
| 2,460,776 A | 2/1949 | Vincent |
| 3,188,165 A | 6/1965 | Magat et al. |
| 3,264,188 A | 8/1966 | Gresham |
| 3,691,271 A | 9/1972 | Charle et al. |
| 3,896,807 A | 7/1975 | Buchalter |
| 4,190,643 A | 2/1980 | Watson et al. |
| 4,309,469 A | 1/1982 | Varona |
| 4,319,956 A | 3/1982 | Snyder et al. |
| 4,362,781 A | 12/1982 | Anderson |
| 4,462,981 A | 7/1984 | Smith |
| 4,481,243 A | 11/1984 | Allen |
| 4,559,157 A | 12/1985 | Smith et al. |
| 4,690,821 A | 9/1987 | Smith et al. |
| 4,690,825 A | 9/1987 | Won |
| 4,764,418 A | 8/1988 | Kuenn et al. |
| 4,786,367 A | 11/1988 | Bogart et al. |
| 4,788,060 A | 11/1988 | Endicott et al. |
| 4,824,689 A | 4/1989 | Kuenn et al. |
| 4,882,221 A | 11/1989 | Bogart et al. |
| 4,883,475 A | 11/1989 | Bogart et al. |
| 4,943,350 A | 7/1990 | Bogart et al. |
| 4,944,938 A * | 7/1990 | Potini .................. 424/68 |
| 5,043,155 A * | 8/1991 | Puchalski et al. ......... 424/78 |
| 5,048,589 A | 9/1991 | Cook et al. |
| 5,164,046 A | 11/1992 | Ampulski et al. |
| 5,246,546 A | 9/1993 | Ampulski |
| 5,252,332 A | 10/1993 | Goldstein |
| 5,334,388 A | 8/1994 | Hoang et al. |
| 5,336,212 A | 8/1994 | De Francesco |
| 5,399,412 A | 3/1995 | Sudall et al. |
| 5,407,958 A | 4/1995 | Heath et al. |
| 5,510,001 A | 4/1996 | Hermans et al. |
| 5,525,345 A | 6/1996 | Warner et al. |
| 5,558,873 A | 9/1996 | Funk et al. |
| 5,585,104 A | 12/1996 | Ha et al. |
| 5,591,309 A | 1/1997 | Rugowski et al. |
| 5,593,508 A * | 1/1997 | Gatt et al. .................. 134/40 |
| 5,601,871 A | 2/1997 | Krzysik et al. |
| 5,614,293 A | 3/1997 | Krzysik et al. |
| 5,624,676 A | 4/1997 | Mackey et al. |
| 5,648,083 A | 7/1997 | Blieszner et al. |
| 5,650,218 A | 7/1997 | Krzysik et al. |
| 5,661,119 A * | 8/1997 | Hersh et al. ............. 510/139 |
| 5,665,364 A | 9/1997 | McAtee et al. |
| 5,665,426 A | 9/1997 | Krzysik et al. |
| 5,686,089 A | 11/1997 | Mitra et al. |
| 5,705,164 A * | 1/1998 | Mackey et al. ............ 424/400 |
| 5,716,692 A | 2/1998 | Warner et al. |
| 5,720,966 A | 2/1998 | Ostendorf |

(Continued)

FOREIGN PATENT DOCUMENTS

CA 1113738 12/1995

(Continued)

*Primary Examiner*—Sreeni Padmanabhan
*Assistant Examiner*—Gina Yu
(74) *Attorney, Agent, or Firm*—Dority & Manning, P.A.

(57) ABSTRACT

A paper product that is applied with a water-soluble lotion composition is provided. In one embodiment of the present invention, the lotion composition includes water in an amount up to about 90% by weight of said lotion composition, a water-soluble skin-conditioning component in an amount up to about 75% by weight of said lotion composition, a viscosity modifier component in an amount up to about 10% by weight of said lotion composition, and an optional liquid-coupling component in an amount up to about 60% by weight of said lotion composition. Typically, the add-on level of the lotion composition is between about 1% to about 25% by weight of the paper product. As a result, the paper product can be used to dry the hands of a user, while also imparting certain benefits to the skin as well.

26 Claims, No Drawings

U.S. PATENT DOCUMENTS

| | | | |
|---|---|---|---|
| 5,728,389 A * | 3/1998 | Sebillotte-Arnaud | 424/400 |
| 5,756,079 A * | 5/1998 | Cauwet et al. | 424/70.19 |
| 5,811,111 A | 9/1998 | McAtee et al. | |
| 5,830,487 A * | 11/1998 | Klofta et al. | 424/402 |
| 5,869,075 A | 2/1999 | Krzysik | |
| 5,871,763 A * | 2/1999 | Luu et al. | 424/402 |
| 5,885,697 A | 3/1999 | Krzysik et al. | |
| 5,891,835 A | 4/1999 | Vlasblom | |
| 5,916,568 A | 6/1999 | Smyth et al. | |
| 5,928,631 A * | 7/1999 | Lucas et al. | 424/65 |
| 5,935,383 A | 8/1999 | Sun et al. | |
| 5,942,240 A | 8/1999 | Merianos et al. | |
| 5,942,479 A | 8/1999 | Frankenbach et al. | |
| 5,948,416 A | 9/1999 | Wagner et al. | |
| 5,951,991 A | 9/1999 | Wagner et al. | |
| 5,962,001 A | 10/1999 | Rose et al. | |
| 5,976,555 A | 11/1999 | Liu et al. | |
| 6,001,377 A | 12/1999 | SaNogueira, Jr. et al. | |
| 6,013,271 A | 1/2000 | Doughty et al. | |
| 6,015,763 A | 1/2000 | Vlasblom | |
| 6,017,417 A | 1/2000 | Wendt et al. | |
| 6,025,431 A | 2/2000 | Cardinali et al. | |
| 6,046,378 A | 4/2000 | Quincy, III et al. | |
| 6,054,020 A | 4/2000 | Goulet et al. | |
| 6,074,527 A | 6/2000 | Hsu et al. | |
| 6,093,410 A | 7/2000 | Peffly et al. | |
| 6,096,325 A | 8/2000 | Date et al. | |
| 6,107,537 A | 8/2000 | Elder et al. | |
| 6,120,783 A * | 9/2000 | Roe et al. | 424/402 |
| 6,149,934 A | 11/2000 | Krzysik et al. | |
| 6,153,208 A * | 11/2000 | McAtee et al. | 424/402 |
| 6,156,157 A | 12/2000 | Schroeder et al. | |
| 6,187,695 B1 | 2/2001 | Krzysik et al. | |
| 6,190,678 B1 | 2/2001 | Hasenoehrl et al. | |
| 6,200,594 B1 | 3/2001 | Ernest et al. | |
| 6,204,208 B1 | 3/2001 | Krzysik et al. | |
| 6,207,596 B1 * | 3/2001 | Rourke et al. | 442/123 |
| 6,217,889 B1 * | 4/2001 | Lorenzi et al. | 424/401 |
| 6,238,682 B1 * | 5/2001 | Klofta et al. | 424/402 |
| 6,267,959 B1 | 7/2001 | Fukushima | |
| 6,267,975 B1 | 7/2001 | Smith, III et al. | |
| 6,280,757 B1 * | 8/2001 | McAtee et al. | 424/402 |
| 6,294,186 B1 * | 9/2001 | Beerse et al. | 424/405 |
| 6,296,862 B1 | 10/2001 | Paul et al. | |
| 6,316,013 B1 | 11/2001 | Paul et al. | |
| 6,380,456 B1 | 4/2002 | Goldman | |
| 6,440,437 B1 * | 8/2002 | Krzysik et al. | 424/402 |
| 6,475,197 B1 | 11/2002 | Krzysik et al. | |
| 6,482,422 B1 | 11/2002 | Paul et al. | |
| 6,485,733 B1 | 11/2002 | Huard et al. | |
| 6,503,525 B1 | 1/2003 | Mayberry et al. | |
| 6,503,526 B1 | 1/2003 | Krzysik et al. | |
| 6,515,029 B1 | 2/2003 | Krzysik et al. | |
| 6,517,848 B1 | 2/2003 | Huard et al. | |
| 6,521,240 B1 | 2/2003 | Minerath, III et al. | |
| 6,521,241 B1 | 2/2003 | Minerath, III et al. | |
| 6,521,242 B1 | 2/2003 | Minerath, III et al. | |
| 6,534,074 B2 | 3/2003 | Krzysik et al. | |
| 6,544,386 B1 | 4/2003 | Krzysik et al. | |
| 2001/0018068 A1 * | 8/2001 | Lorenzi et al. | 424/443 |

FOREIGN PATENT DOCUMENTS

| | | |
|---|---|---|
| DE | 3416043 A | 10/1985 |
| DE | 4202703 A1 | 9/1993 |
| EP | 613675 A1 | 9/1994 |
| EP | 365160 B1 | 12/1994 |
| EP | 808157 B1 | 11/1997 |
| EP | 0870496 A2 | 10/1998 |
| WO | WO 9321383 | 10/1993 |
| WO | 9405856 | 3/1994 |
| WO | WO 9614835 A1 | 5/1996 |
| WO | 9803147 | 1/1998 |
| WO | WO 9921532 A1 | 5/1999 |
| WO | 9941068 | 8/1999 |
| WO | 9945971 | 9/1999 |
| WO | WO0064408 A1 | 11/2000 |

* cited by examiner

WATER-SOLUBLE LOTIONS FOR PAPER PRODUCTS

BACKGROUND OF THE INVENTION

Absorbent paper products, such as hand towels are commonly used to absorb fluids applied to the skin of a user during hand washing. The paper products are designed to absorb fluids from the skin and leave the skin dry. However, the soap ingredients often used to cleanse a person's hands or skin can remove oils, lipids, and natural skin conditioners and moisturizers from the stratum corneum of the person, leaving the skin excessively dry and subject to various skin problems, such as erythema, scales, flakes, and fissures. In addition, many people commonly wash their hands in environments susceptible to various diseases caused by the spread or growth of microbes, such as bacteria and viruses.

As such, a need currently exists for a paper product that contains a formulation that can readily transfer to the user's skin to inhibit excessive dryness and other related skin problems.

SUMMARY OF THE INVENTION

The present invention is directed to a paper product that can dry and condition the skin of a user. In accordance with one embodiment of the present invention, a water-soluble lotion composition is applied to the paper product. The lotion composition contains water in an amount up to about 90% by weight of the lotion composition, a water-soluble skin conditioning component in an amount up to about 75% by weight of the lotion composition and a viscosity modifier component in an amount up to about 10% by weight of the lotion composition. Typically, the add-on level of the lotion composition is between about 1% to about 25% by weight of the paper product.

For example, in one embodiment of the present invention, the lotion composition applied to the paper product includes water in an amount between about 10% to about 30% by weight of the lotion composition. In this embodiment, the lotion composition also contains a water-soluble skin conditioning component in an amount between about 10% to about 40% by weight of the lotion composition. For example, the water-soluble skin conditioning component can include, glycerin, propylene glycol, sorbitol, or combinations thereof. Further, a viscosity modifier component can also be utilized in an amount between about 2% to about 5% by weight of the lotion composition. For example, the viscosity modifier component can include a surfactant that increases the viscosity of the lotion, such as talloweth-60-myristyl glycol.

In accordance with another embodiment of the present invention, a process for producing a paper product for drying and conditioning the skin of a user is disclosed. The process includes forming a fibrous web, through-drying the web to remove water therefrom, and thereafter treating the dried web with a lotion composition such that the lotion has an add-on level of between about 1% to about 10% by weight of said paper product. For example, in some embodiments, the lotion composition can be printed onto the paper web. In other embodiments, the lotion composition can also be sprayed onto the paper web.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to a paper product that contains a lotion useful for treating a person's skin. In particular, the lotion is a water-soluble lotion that contains water, a water-soluble skin conditioning component, a viscosity modifier component, an optional liquid-coupling component, and various other ingredients, such as anti-microbial agents, preservatives, etc. It has been discovered that the particular selection and amount of ingredients utilized in the lotion of the present invention can provide a synergistic effect when applied to a paper product. Moreover, it has also been discovered that the lotion of the present invention can be applied at relatively low add-on levels to a paper product such that the resulting paper product can remain absorbent. As a result, the paper product of the present invention can dry a person's skin after washing, while simultaneously imparting certain benefits to the skin, such as inhibiting microbial growth, skin disease, skin dryness, etc.

Paper products made in accordance with the present invention can include various types of products, such as towels, wipes, napkins, facial and bath tissue, and the like. The paper product can generally be produced from paper webs having one or multiple layers. Moreover, depending on the desired characteristics, the paper product can contain one or multiple plies where each ply can contain one or more layers. The basis weight of the paper products can vary dependent on the particular application. In some embodiments, for example, the paper product can have a basis weight from about 1 to about 50 pounds per 2,880 square feet (i.e., ream), and in some embodiments, between about 5 to about 45 pounds per square ream. For instance, paper towels can sometimes be formed to have a basis weight of from about 10 to about 45 pounds per ream, and in some embodiments, between about 20 to about 30 pounds per ream. Suitable cellulosic fibers for use in connection with this invention include secondary (recycled) papermaking fibers and virgin papermaking fibers in all proportions. Such fibers include, without limitation, hardwood and softwood fibers as well as nonwoody fibers. Noncellulosic synthetic fibers can also be included as a portion of the furnish. It has been found that a high quality product having a unique balance of properties can be made using predominantly secondary fibers or all secondary fibers.

As stated above, the paper product of the present invention is applied with a lotion that is water-soluble. The term "water-soluble" refers to a compound that has a hydrophilic-lipophilic balance (HLB) number of 7 or greater. The HLB index is well known in the art and is a scale that measures the balance between the hydrophilic and lipophilic solution tendencies of a compound. The HLB scale ranges from 1 to approximately 100, with the lower numbers representing highly lipophilic tendencies and the higher numbers representing highly hydrophilic tendencies.

In general, the amount of water utilized in the present invention can vary depending on the desired characteristics of the paper product. For example, in some embodiments, water can be utilized in an amount up to about 90% by weight of the composition, in some embodiments, up to about 50% by weight of the composition, and in some embodiments, between about 10% to about 30% by weight of the composition.

In addition to containing water, the water-soluble lotion composition can also contain a variety of other ingredients. For instance, the water-soluble lotion can contain a water-soluble skin conditioning component that includes one or more water-soluble skin conditioning agents. A water-soluble skin conditioning component can provide a number of benefits to the lotion of the present invention. For example, a lotion applied to a paper product can be transferred to a person's hand after use. The water-soluble skin conditioning component of the lotion can enhance the retention of moisture on the person's skin and inhibit transepidermal water loss, even after the person uses the paper product. By retaining water, a user's skin will be less prone to becoming excessively dry, as well as being inhibited from developing certain skin problems, such as erythema. Moreover, the water-soluble skin conditioning component can also contain ingredients that can help to maintain the soft, smooth, and pliable appearance and feel of the skin.

The amount of the water-soluble skin conditioning component can generally vary. For example, in some embodiments, the amount of the water-soluble skin conditioning component can be up to about 75% by weight of the lotion composition, in some embodiments up to about 40% by weight of the composition, and in some embodiments, between about 10% to about 40% by weight of the composition.

In general, a variety of water-soluble skin conditioning agents may be suitable for use in the present invention. For instance, some suitable water-soluble skin conditioning agents include, but are not limited to, allantoin; polydimethyl siloxanes, such as polysiloxane ethers and organobetaines and dimethicone copolyol benzoate; amino acids, such as collagen, potassium lauryl wheat, silk, cocodimonium hydroxypropyl silk, and keratin; monoethanol amines (MEA), such as acetamide and lactamide; quaternized materials, such as cetyl trimethyl ammonium chloride, stearyl dimethyl benzyl ammonium chloride, stearamidopropyl dimethyl myristyl acetate ammonium chloride, cationic cellulose, quaternium 75, canolamidopropyl ethyldimonium ethosulfate, linoleamidopropyl ethyldimonium ethosulfate, behentrimonium methosulfate, guar hydroxypropyl trimonium chloride, castor oil quaternary compounds, polyquaternium 10, coco phosphatidyl PG-dimonium chloride, and sodium borageamidopropyl PG-dimonium chloride phosphate; collagen proteins, such as hydrolyzed collagen, cocodimonium hydrolyzed collagen, hydrolyzed elastin, hydrolyzed wheat protein, hydrolyzed silk, hydrolyzed rice protein, hydrolyzed wool keratin, and hydrolyzed mild protein; surfactants, such as sodium lauroyl sarcosinate, PPG-5 ceteth-10 phosphate, cetyl betaine, isostearamidopropyl morpholine lactate, behenamine oxide, wheat germamidopropyl betaine, disodium wheat germamido PEG-2 sulfosuccinate, sodium isostearoyl-2 lactylate, calcium stearoyl lactylate, sodium stearoyl lactylate, and sodium lauroyl lactylate; ethyl panthenol; hydrolyzed oats; hyaluronic acid and salts thereof, such as sodium hyaluronate; polysaccarides, such as sodium carboxymethyl beta glucan; ethoxylated oils, such as PEG-10 and PEG-5 soy sterol, PEG-24 hydrogenated lanolin, Laneth-5, Laneth-15, PEG-75 lanolin, PEG-65 lanolin, PEG-7 glyceryl cocoate, PEG-6 caprylic/capric glycerides, PEG-20 almond glycerides, PEG-60 almond glycerides, PEG-20 corn glycerides, PEG-40 castor oil, PEG-80 castor oil, and PEG-80 glyceryl cocoate; ethoxylated and propoxylated glucose derivatives, such as Glucam E-10, Glucam E-20, Glucam P-10, polyethylene oxides, such as PEG-2000, PEG-9, PEG-23, PEG-45, and PEG-90; aloe Vera; and the like.

In addition to the water-soluble skin conditioning agents mentioned above, other skin conditioning agents may also be suitable for use in the present invention. For example, in one embodiment, the skin conditioning component can include a humectant (i.e., a compound that has an affinity for water). A humectant can generally provide a number of benefits to a lotion of the present invention. For example, as stated above, a humectant, which has an affinity for water, can further enhance the retention of moisture on the person's skin and inhibit transepidermal water loss.

In general, a variety of humectants may be suitable for use in the present invention. For instance, some suitable water-soluble humectants include, but are not limited to, glycerin; ethoxylated glycerins, such as POE-26 glycerine, POE-7 glycerin, sorbitol, 1,2,6-hexanetriol sorbitol, and hydroxypropyl sorbitol; phosphinic carboxylic acid (PCA) and salts thereof, such as sodium PCA; alpha hydroxy acids and salts thereof, such as lactic acid, sodium lactate, and glycolic acid; glucose derivatives, such as glucose glutamate; polyalkylene glycols and alkylene polyols and their derivatives, including propylene glycol, dipropylene glycol, polypropylene glycol, polyethylene glycol, 1,3-butylene glycol, triethylene glycol, and dipropylene glycol; and other water-soluble humectants, such as maltodextrin, maltitol, mannitol, zylitol, sodium polyaspartate, ethoxylated castor oil, various humectants available from Lipo Chemicals (e.g., acetamide MEA, ethoxylated glycerin, lactamide MEA, etc.), and the like. For instance, the inventors of the present invention have discovered that glycerin may be particularly useful in moisturizing the skin of a user and protecting it from excessive drying and other problems with the skin.

For instance, in one embodiment, the inventors of the present invention have discovered that a water-soluble skin-conditioning component containing glycerin, propylene glycol, and/or sorbitol may be particularly useful in moisturizing the skin of a user and protecting it from excessive drying and other problems with the skin. For example, in some embodiments, the amount of glycerin can be up to about 25% by weight of the lotion composition, in some embodiments up to about 15% by weight of the composition, and in some embodiments, between about 2% to about 15% by weight of the composition. Further, in some embodiments, the amount of propylene glycol can be up to about 30% by weight of the lotion, and in some embodiments, between about 5% to about 20% of the lotion. Moreover, in some embodiments, the amount of sorbitol can be up to about 30% by weight of the lotion, and in some embodiments, between about 5% to about 20% of the lotion.

In some embodiments, a viscosity modifier component that includes one or more viscosity modifiers may also be utilized in the lotion composition. In particular, viscosity modifiers can be used to increase the viscosity of (i.e., thicken) the water-soluble lotion such that it can be better retained on the surface of the paper product. For example, in some embodiments, the amount of the viscosity modifier component can be up to about 10% by weight of the lotion composition, in some embodiments up to about 5% by weight of the composition, and in some embodiments, between about 2% to about 5% by weight of the composition.

Some examples of suitable viscosity modifiers can include, but are not limited to, cellulosic derivatives, polyalkylene glycols, polyvinyl alcohol, sodium polyacrylate and other water-soluble macromolecules, etc. In addition to thickening the lotion composition, the viscosity modifier can also clean and/or moisturize the skin of a user. For example, some viscosity modifiers that may also condition the skin of a user can include certain surfactants, such as, but not limited to, PEG-80 glyceryl cocoate, behentrimonium methosulfate and cetearyl alcohol, PEG-2000, sodium stearoyl lactylate, PEG-75 lanolin, and the like. Moreover, in one embodiment, the present inventors have discovered that alkyoxylated alcohol surfactants, such as talloweth-60-myristyl glycol (sold under the name Elfacos® GT-282S by Akzo Nobel), can be particularly useful in thickening the water-soluble lotion and in cleaning and/or moisturizing the skin of a user. Other suitable viscosity modifiers may also be described in U.S. Pat. No. 6,025,431 to Cardinali, et al., which is incorporated herein in its entirety by reference thereto for all purposes.

In addition to the above-mentioned components, an optional liquid-coupling component that includes one or more liquid-coupling agents can also be utilized. For instance, liquid-coupling agents can be used to couple the ingredients of the composition together to ensure that the lotion composition does not separate into more than one liquid phase. As a result, the ingredients of the lotion composition can be more uniformly applied to the skin of a user. In some embodiments, a liquid-coupling surfactant can also aid in solubilizing certain ingredients, such as antimicrobial agents. The liquid-coupling agent(s) may or may not also act as a viscosity modifier and/or as a skin conditioning agent.

When utilized, the amount of the liquid-coupling component can generally vary. For example, in some embodiments, the amount of the liquid-coupling component can be up to about 60% by weight of the lotion composition, in some embodiments up to about 50% by weight of the composition, and in some embodiments, between about 20% to about 40% by weight of the composition.

A variety of liquid-coupling agents may be utilized in the present invention. For example, various surfactants may be utilized within the liquid-coupling component. For instance, some nonionic surfactants that can be used in the present invention include, but are not limited to, an alkoxylated fatty acid (e.g., DI600® from High Point Chemical Corp), alkyl phenyl ethers of polyethylene glycol (e.g., Union Carbide's Tergitol® series of surfactants), alkylphenolethylene oxide condensation products (e.g., Rhone Poulenc, Incorporated's Igepal® series of surfactants), and aryl alkyl polyether alcohols (e.g., Rohm and Haas's Triton® series of surfactants, such as Triton® X-100), Calgon Corporation's ORLENE® series surfactants, such as ORLENE® 1070, 1071, 1084 and 1060; alkyl polyglycosides (APG) derived as a condensation product of dextrose (D-glucose) and a straight or branched chain alcohol (e.g., Horizon Chemical's APG Series, such as APG-300, APG-350, and APG-500).

In some cases an anionic surfactant may also be used. For instance, one type of anionic surfactant that can be utilized is a water-soluble sulfated and sulfonated anionic alkali metal and alkaline earth metal detergent salts containing a hydrophobic higher alkyl moiety (typically containing from about 8 to 22 carbon atoms), such as salts of higher alkyl mono or polynuclear aryl sulfonates having from about 1 to 16 carbon atoms in the alkyl group, with examples available as the Bio-Soft series, i.e., Bio-Soft D-40 (Stepan Chemical Co.).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides, such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$–$C_{16}$ alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a $C_{12}$–$C_{15}$ n-alkanol, i.e., the Neodol ethoxysulfates, Shell Chemical Co.); alkali metal salts of higher fatty esters of low molecular weight alkylol sulfonic acids, e.g., fatty acid esters of the sodium salt of isothionic acid, the fatty ethanolamide sulfates; the fatty acid amides of amino alkyl sulfonic acids, e.g., lauric acid amide of taurine; as well as numerous other anionic organic surfactants, such as sodium xylene sulfonate, sodium naphthalene sulfonate, sodium toluene sulfonate, and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surfactants can be employed in the form of their alkali metal salts, ammonium or alkaline earth metal salts. Another example of a suitable anionic surfactant includes an amino-acid based surfactant, such as acylglutamate, which is marketed under the name "Amisoft" by Ajinomoto Corp., Tokyo, Japan.

Still other examples of suitable anionic surfactants include, but are not limited to, ammonium or sodium salts of a sulfated ethoxylate derived from a 12 to 14 carbon linear primary alcohol such as Vista's Alfonic® 1412A or 1412S; and, sulfonated naphthalene formaldehyde condensates, (e.g., Rohm and Haas's Tamol® SN).

Further, in some instances, a cationic surfactant can also be used. Suitable cationic surfactants can include, but are not limited to, CIBA-GEIGY's Amasoft® 16-7 and Sapamine® P; Quaker Chemicals' Quaker® 2001; and American Cyanamid's Cyanatex®. Other suitable surfactants are described in U.S. Pat. No. 5,830,487 to Klofta, et al., which is incorporated herein in their entirety by reference thereto for all purposes. Moreover, as stated above, various blends of surfactants can be utilized in some instances. For instance, in one embodiment, a blend of surfactants obtained from Rhodia under the name Extra Blend DV-6161 can be utilized.

As stated above, various other ingredients may also be utilized in the lotion composition of the present invention. For instance, in some embodiments, an antimicrobial agent (i.e., an additive that is capable of killing viruses, bacteria, fungi, and other microbes) can be incorporated into the lotion composition to disinfect a user's skin and/or to inhibit the further spread of certain microbes. Typically, an antimicrobial agent utilized in the present invention is biocompatible. The antimicrobial agent can also be water-soluble or capable of being solubilized by an ingredient of the lotion composition. For example, some suitable antimicrobial agents that can be used in the present invention include, but are not limited to, chlorohexidine gluconate; parachlorometaxylenol (PCMX); benzylthoneium chloride; chitosan, such as chitosan pyrrolidone carboxylate; 2,4,4'-trichloro-2'-hydroxydiphenyl ether (triclosan), etc. Other suitable antimicrobial agents are described in U.S. Pat. No. 5,871,763 to Luu, et al., U.S. Pat. No. 5,334,388 to Hoang, et al., and U.S. Pat. No. 5,686,089 to Mitra, et al., which are incorporated herein in their entirety by reference thereto for all purposes.

The amount of an antimicrobial agent(s) utilized in the lotion composition of the present invention can generally vary. For example, in some embodiments, the amount of the antimicrobial agent(s) can be up to about 20% by weight of the composition, in some embodiments up to about 10% by weight of the composition, and in some embodiments, between about 0.01% to about 5% by weight of the composition.

Furthermore, in some embodiments, the lotion can also contain one or more preservatives. The preservative(s) can inhibit the growth of certain microbes on the paper product before and/or after use. Moreover, when the lotion composition is transferred to the skin of a user, the preservative(s) can further inhibit the growth of microbes thereon. The amount of the preservative(s) utilized in the lotion composition of the present invention can generally vary. For example, in some embodiments, the amount of the preservative(s) can be up to about 5% by weight of the composition, in some embodiments up to about 3% by weight of the composition, and in some embodiments, between about 0.1% to about 2% by weight of the composition.

Some suitable preservatives that can be used in the present invention include, but are not limited to, Mackstat H 66 (available from McIntyre Group, Chicago, Ill.), DMDM hydantoin (e.g., Glydant Plus™, Lonza, Inc., Fair Lawn, N.J.), iodopropynyl butylcarbonate, Kathon (Rohm and Hass, Philadelphia, Pa.), methylparaben, propylparaben, 2-bromo-2-nitropropane-1,3-diol, benzoic acid, amidazolidinyl urea, diazolidinyl urea, and the like. Moreover, in one particular embodiment, a preservative obtained under the name "Phenonip" from NIPA Hardwick can be utilized. Other suitable preservatives includes those sold by Sutton Labs, such as "Germall 115" (amidazolidinyl urea), "Germall II" (diazolidinyl urea), and "Germall Plus" (diazolidinyl urea and iodopropynyl butylcarbonate).

In order to better enhance the benefits to consumers, other ingredients can also be used. For instance, some classes of ingredients that can be used include, but are not limited to: antiacne actives (a drug product used to reduce the number of acne blemishes, acne pimples, blackheads, and whiteheads); antifoaming agents (reduce the tendency of foaming during processing); antiseptic actives; antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); solvents (e.g., hexylene glycol); and sunscreens (ingredients that absorb at least 85 percent of the light in the UV range at wavelengths from 290 to 320 nanometers, but transmit UV light at wavelengths longer than 320 nanometers). For instance, in one embodiment, Aloe Vera powder can be utilized in an amount between about 0.0005% to about 0.005% by weight of the lotion composition.

Although various ingredients have been separately described herein, it should be understood that one ingredient may completely or partially accomplish the function of more than one ingredient. For example, the viscosity modifier component may contain an ingredient, such as a surfactant, that thickens the solution and also acts as an ingredient of the liquid-coupling component and/or the water-soluble skin conditioning component to enhance the uniform application of the lotion and/or to moisturize the skin.

Once formed, the lotion composition described above can then be applied to the paper product. The paper product may be formed from any papermaking process known in the art. For example, a papermaking process of the present invention can utilize creping, embossing, wet-pressing, double creping, calendering, as well as other known steps in forming the paper web. One particular embodiment of the present invention utilizes a non-compressive drying technique, such as uncreped through-drying, to form the paper product. In some instances, an uncreped through-dried paper product may have good absorbency and wet-resiliency characteristics. Some examples of uncreped through-drying techniques are disclosed in U.S. Pat. No. 5,048,589 to Cook, et al.; U.S. Pat. No. 5,399,412 to Sudall, et al.; U.S. Pat. No. 5,510,001 to Hermans, et al.; U.S. Pat. No. 5,591,309 to Rugowski, et al.; and U.S. Pat. No. 6,017,417 to Wendt, et al., which are incorporated herein in their entirety by reference thereto for all purposes.

For example, uncreped through-drying generally involves the steps of: (1) forming a furnish of cellulosic fibers, water, and optionally, other additives, such as debonders and wet-strength agents; (2) depositing the furnish on a traveling foraminous belt, thereby forming a fibrous web on top of the traveling foraminous belt; (3) subjecting the fibrous web to through-drying to remove the water from the fibrous web; and (4) removing the dried fibrous web from the traveling foraminous belt.

In some embodiments, once the paper web is dried, the lotion composition described above can then be applied. In general, the lotion composition of the present invention can be applied to the paper product using a variety of methods. For instance, in one embodiment, the composition can be applied to the surface of the paper product using rotogravure printing, either direct or indirect (offset). Rotogravure printing can sometimes offer better control of the distribution and transfer rate of the composition onto the paper product. In addition, other application methods, such as flexographic printing, spraying (e.g., WEKO), hot melt adhesive spraying (e.g., Nordson), blade, saturant, coating, droplet throw, and foam applications, can be used.

Further, the lotion composition can be applied to one or both outer surfaces of the product after the product has been dried. When utilizing a multi-ply paper product, the lotion composition can be applied after the plies are brought together or prior to bringing the plies together. The individual plies can be layered or blended (homogeneous), creped or uncreped, through-dried or wet-pressed. In one embodiment, for example, the paper product is an uncreped through-dried paper product.

Other methods of applying the lotion to a paper product can also be utilized. For example, some ingredients of the lotion can be first entrapped within a porous delivery vehicle before being applied to the paper product such that the ingredients can be controllably released during drying and after the lotion is transferred to a user's skin. For instance, some delivery vehicles that can be used include, but are not limited to, microsponges, microcapsules, cyclodextrins and their derivatives, liposomes, polymeric sponges, and spray-dried starch. For instance, in some embodiments, the lotion composition may contain microcapsules in an amount of up to about 25% by weight of the lotion, in some embodiments up to about 10% by weight of the lotion, and in some embodiments, between about 0.2% to about 5% by weight of the lotion.

For instance, some examples of "microsponges" are described in U.S. Pat. No. 4,690,825 to Won, which is incorporated herein in its entirety by reference thereto for all purposes. Another delivery vehicle that may be useful is a sponge-like material, such as POLY-PORE® L200. Moreover, one example of a microcapsule that may be suitable for use in the present invention is POLY-PORE® E200 (Chemdal Corp., Arlington Heights, Ill.), which is a delivery agent having soft, hollow spheres that can contain an additive at over 10 times the weight of the delivery vehicle.

The add-on level of the lotion can generally vary depending on the desired effect of the composition on the product attributes and the specific composition. As used herein, the term "add-on level" refers to the weight of a paper product treated with the lotion composition subtracted by the weight of the product prior to treatment, wherein this calculated weight is divided by the weight of the treated paper product and then multiplied by 100. For example, the add-on level of the composition can be from about 1 to about 25 weight percent, in some embodiments from about 1 to about 10 weight percent, in some embodiments from about 1 to about 6 weight percent, in some embodiments from about 1 to about 5 weight percent, and in some embodiments, from about 1 to about 3 weight percent based on the weight of the paper product.

The present invention may be better understood with reference to the following representative examples.

EXAMPLE 1

The ability to form lotions for use on a paper product in accordance with the present invention was demonstrated. In particular, four lotions labeled A, B, C, and D were formed having the following characteristics:

TABLE 1

Components of the Lotion Compositions

| Ingredient | A (wt. % of lotion) | B (wt. % of lotion) | C (wt. % of lotion) | D (wt. % of lotion) |
|---|---|---|---|---|
| Water* | 10 | 10 | 10 | 10 |
| PEG-80 glyceryl cocoate** | 20 | 20 | 10 | 0 |
| Glycerin* | 20 | 20 | 20 | 20 |
| Propylene glycol* | 20 | 20 | 10 | 10 |

TABLE 1-continued

Components of the Lotion Compositions

| Ingredient | A (wt. % of lotion) | B (wt. % of lotion) | C (wt. % of lotion) | D (wt. % of lotion) |
|---|---|---|---|---|
| PPG-5 ceteth-10 phosphate* | 10 | 0 | 0 | 0 |
| PEG-40 castor oil* | 10 | 10 | 0 | 0 |
| PEG-6 caprylic/capric glycerides* | 10 | 10 | 10 | 10 |
| behentrimonium methosulfate and cetearyl alcohol** | 0 | 10 | 20 | 0 |
| PEG-60 almond glycerides* | 0 | 0 | 10 | 10 |
| PEG-2000** | 0 | 0 | 10 | 10 |
| Sodium stearoyl lactylate** | 0 | 0 | 0 | 20 |
| PEG-75 lanolin** | 0 | 0 | 0 | 10 |

*These ingredients were provided as a liquid at room temperature.
**These ingredients were provided as a solid at room temperature.

For each sample, the liquid ingredients were first mixed together. Once mixed, the liquid mixture was then heated to 70° C. and stirred while the remaining solid ingredients were added. Stirring was continued until all of the ingredients were dissolved. Thereafter, the lotion was allowed to cool to room temperature while being stirred. The resulting lotion was then applied to an uncreped through-dried hand towel using a liquid dropping device until the resulting add-on level was 7% by weight of the hand towel.

The towel was formed from recycled fibers in an amount of 50% by weight of the web and from Pictou northern softwood fibers in an amount of 50% by weight of the web. The Pictou fibers were refined for 8 minutes using conventional refining techniques. The furnishes were then supplied to a machine chest and blended. A Kymene® 557H wet strength agent was also added to the machine chest in an amount of 20 pounds per ton. Further, a Witco C-6001 imidazoline-based softener was applied to the machine chest thereafter in an amount of 1.5 pounds per ton. The fibrous furnish was then formed into a paper web and dried using a through-air dryer. The resulting hand towel had a basis weight of 25 pounds per ream.

EXAMPLE 2

The ability to form a paper product to condition the skin of a user was demonstrated. A lotion was first formed having the following composition:

TABLE 2

Components of the Lotion Composition

| Component | Weight % of the Composition |
|---|---|
| Water | 16.3575 |
| Elfacos ® GT-282S | 3.1800 |
| Hexylene Glycol | 19.9800 |
| Propylene Glycol | 19.9800 |
| Phenonip | 0.5000 |
| PCMX | 1.0000 |
| Extra Blend (DV-6161) | 39.0000 |
| Aloe Vera Powder | 0.0025 |

The lotion composition was formed by first providing purified water at a temperature between 170° F. to 180° F. Thereafter, each of the ingredients was sequentially applied (as listed in descending order in Table 2) to the water and mixed until the lotion composition was achieved. Thereafter, the resulting lotion was printed onto an uncreped through-dried hand towel such that the resulting add-on level was 4% by weight of the hand towel. The towel was formed as described in Example 1.

EXAMPLE 3

The ability to form a paper product to condition the skin of a user was demonstrated. A lotion was first formed having the following composition:

TABLE 3

Components of the Lotion Composition

| Component | Weight % of the Composition |
|---|---|
| Water | 16.3575 |
| Elfacos ® GT-282S | 3.1800 |
| Hexylene Glycol | 19.9800 |
| Glycerin | 19.9800 |
| Phenonip | 0.5000 |
| PCMX | 1.0000 |
| Extra Blend (DV-6161) | 39.0000 |
| Aloe Vera Powder | 0.0025 |

The lotion composition was formed by first providing purified water at a temperature between 170° F. to 180° F. Thereafter, each of the ingredients was sequentially applied (as listed in descending order in Table 3) to the water and mixed until the lotion composition was achieved. Thereafter, the resulting lotion was printed onto an uncreped through-dried hand towel such that the resulting add-on level was 4% by weight of the hand towel. The towel was formed as described in Example 1.

EXAMPLE 4

The ability of a paper product to condition the skin of a user during drying was demonstrated. A lotion was first formed having the following composition:

TABLE 4

Components of the Lotion Composition

| Component | Weight % of the Composition |
|---|---|
| Water | 16.3575 |
| Elfacos ® GT-282S | 3.1800 |
| Hexytene Glycol | 19.9800 |
| Propylene Glycol | 16.9800 |
| Glycerin | 3.0000 |
| Phenonip | 0.5000 |
| PCMX | 1.0000 |
| Extra Blend (DV-6161) | 39.0000 |
| Aloe Vera Powder | 0.0025 |

The lotion composition was formed by first providing purified water at a temperature between 170° F. to 180° F. Thereafter, each of the ingredients was sequentially applied (as listed in descending order in Table 4) to the water and mixed until the lotion composition was achieved. Thereafter, the resulting lotion was printed onto an uncreped through-dried hand towel such that the resulting add-on level was 4% by weight of the hand towel. The towel was formed as described in Example 1.

After forming the hand towel, the properties of the hand towel of the present invention were compared to an untreated hand towel using a panel of health care professionals according to the following procedure where the code 435 represents the untreated sample and the code 258 represents the treated sample.

Procedure:

Thank you for participating in a use test to determine the hand-feel and physical properties of lotionized hand towels. You will be evaluating two sets of hand towels that may or may not contain lotion. Please use both hand towels and remember what your hands feel like after each use before completing the questionnaire.

This is a direct paired comparison study. Please compare your evaluations of the second towel with the first one when completing the questionnaire for the second one.

1. Please wash your hands six times with 1 pump of Bacti-Stat soap and dry your hands each time with a set of towels. Please wait 15 seconds after each hand wash (count to 15 quietly to yourself). A representative will hand you the appropriate hand towel to dry your hands and inform you of the towel code. Record on the questionnaire (Q.1) the number of towels used to completely dry your hands after washes 1 and 6. Please wash, rinse and dry your hands as you normally do at work. Please wait until your hands are completely dry to feel your hands' condition after each drying. The product works best when your hands are completely dry. Also, please pay attention to the performance of the towels during each drying.

2. After the 6th wash, wait 4 minutes. During this time continue to feel your hands together. At the end of 4 minutes, complete question #2 for the appropriate towel code.

3. Please wash your hands six more times with 1 pump of Bacti-Stat soap and dry your hands each time with another different set of towels. Please wait 15 seconds after each hand wash (count to 15 quietly to yourself). Once again, a representative will hand you the appropriate hand towel to dry your hands and inform you of the towel code. Record on the questionnaire (Q.1) the number of towels used to completely dry your hands each time. Please wash, rinse and dry your hands as you normally do at work. Please wait until your hands are completely dry to feel your hands' condition after each drying. The product works best when your hands are completely dry. Also, please pay attention to the performance of the towels during each drying.

4. After six additional washes, please wait 4 minutes. During this time continue to feel your hands together. At the end of 4 minutes, complete question #2 for the appropriate towel code.

5. Complete question #3 on the following survey sheet.

Q.1 Number of towels to completely dry your hands:
    435: 1st ____ 6th ____
    258: 1st ____ 6th ____
Q.2 On a scale from 1–10, where 1 = Very Poor, and 10 = Excellent, please evaluate the following attributes for the two hand towels you have just used.

| How ____ did your hands feel after use? | 435 | 258 |
|---|---|---|
| Lotionized | | |
| Soft | | |
| Smooth | | |
| Silky | | |
| Moisturized | | |

-continued

Irritated (10 = no irritation)
Residue (10 = a lot of residue)

| | 435 | 258 |
|---|---|---|
| How soft did the towel feel during use? | | |
| How effective was the towel in drying your hands? | | |
| How quickly did the towel dry your hands? | | |
| How strong was the towel during use? | | |
| How substantial did the towel feel during use? | | |
| How would you rate the overall quality of the towel? | | |

Q.3 Would either of these towels encourage you to wash your hands more frequently?
Yes   No   Maybe, If yes, which one? _____

Table 5 reflects the percent of those tested who only used the corresponding number of towels to dry their hands after the first and sixth washes for the untreated sample.

TABLE 5

Towel Usage (untreated sample)

| Number of Towels Used | (%) First Wash | (%) Sixth Wash |
|---|---|---|
| 1 | 50.0 | 53.0 |
| 2 | 43.0 | 33.0 |
| 3 | 7.0 | 10.0 |
| 4 | 0.0 | 4.0 |

Table 6 reflects the percent of those tested who only used the corresponding number of towels to dry their hands after the first and sixth washes for the treated sample.

TABLE 6

Towel Usage (treated sample)

| Number of Towels Used | (%) First Wash | (%) Sixth Wash |
|---|---|---|
| 1 | 43.0 | 35.0 |
| 2 | 50.0 | 48.0 |
| 3 | 7.0 | 14.0 |
| 4 | 0.0 | 3.0 |

As illustrated from the tables above, the addition of the lotion composition onto a hand towel did not substantially affect the ability of the towel to dry a person's hands. For example, the percentage of the subjects that needed four towels to dry their hands for the sixth wash actually decreased from 4.0% to 3.0%.

In addition, the hand condition and towel attributes tested are given below in Tables 7 and 8.

TABLE 7

Hand Condition Attributes

| Attribute | % Who Preferred Untreated Towel | % Who Preferred Treated Towel | % Who Perceived No Difference in Samples |
|---|---|---|---|
| Lotionized | 33.0 | 40.0 | 27.0 |
| Softness | 37.0 | 40.0 | 23.0 |

TABLE 7-continued

Hand Condition Attributes

| Attribute | % Who Preferred Untreated Towel | % Who Preferred Treated Towel | % Who Perceived No Difference in Samples |
|---|---|---|---|
| Smoothness | 30.0 | 43.0 | 27.0 |
| Silkiness | 37.0 | 37.0 | 27.0 |
| Moisturization | 43.0 | 27.0 | 30.0 |
| Average | 36.0 | 37.0 | 27.0 |

TABLE 8

Towel Quality

| Attribute | % Who Preferred Untreated Towel | % Who Preferred Treated Towel | % Who Perceived No Difference in Samples |
|---|---|---|---|
| Softness | 26.0 | 37.0 | 37.0 |
| Effectiveness | 33.0 | 40.0 | 27.0 |
| Dryness | 37.0 | 37.0 | 26.0 |
| Strength | 21.0 | 33.0 | 47.0 |
| Substantial | 30.0 | 30.0 | 40.0 |
| Overall Towel Quality | 43.0 | 26.0 | 31.0 |
| Average | 32.0 | 34.0 | 35.0 |

Thus, as indicated from the representative examples above, a paper product of the present invention can provide numerous benefits to a user.

EXAMPLE 5

The ability of a paper product to condition the skin of a user during drying was demonstrated. A lotion was first formed having the following composition:

TABLE 9

Components of the Lotion Composition

| Component | Weight % of the Composition |
|---|---|
| Water | 16.3575 |
| Elfacos ® GT-282S | 3.1800 |
| Hexylene Glycol | 19.9800 |
| Propylene Glycol | 16.9800 |
| Glycerin | 3.0000 |
| Phenonip | 0.5000 |
| PCMX | 1.0000 |
| Extra Blend (DV-6161) | 39.0000 |
| Aloe Vera Powder | 0.0025 |

The lotion composition was formed by first providing purified water at a temperature between 170° F. to 180° F. Thereafter, each of the ingredients was sequentially applied (as listed in descending order in Table 9) to the water and mixed until the lotion composition was achieved. Thereafter, the resulting lotion was printed onto an uncreped through-dried hand towel such that the resulting add-on level was 4% by weight of the hand towel. The towel was formed as described in Example 1.

After forming the hand towel, the properties of the hand towel of the present invention were compared to an untreated hand towel the following procedure. Initially, 39 health care professionals washed their hands one time with "Bacti-Stat" Soap and made an initial hand condition rating.

Thereafter, the subjects then washed their hands six additional times and a technician dried one hand with the treated towel and the other hand with an untreated towel. The subjects were then asked to compare the overall hand feel of each towel by answering a survey, such as set forth above in the first survey form of Q2 in Example 4.

After a five-minute waiting period, the subjects again washed their hands six additional times and a technician dried one hand with the treated towel and the other hand with an untreated towel.

The hand condition attributes for each set of washes are given below in Tables 10 and 11.

TABLE 10

Hand Condition Attributes After Six Washes

| Attribute | % Who Preferred Untreated Towel | % Who Preferred Treated Towel | % Who Perceived No Difference in Samples |
|---|---|---|---|
| Lotionized | 23.0 | 44.0 | 33.0 |
| Softness | 21.0 | 36.0 | 44.0 |
| Smoothness | 21.0 | 44.0 | 36.0 |
| Silkiness | 18.0 | 44.0 | 38.0 |
| Moisturization | 24.0 | 39.0 | 37.0 |
| Overall | 18.0 | 51.0 | 31.0 |

TABLE 11

Hand Condition Attributes After Twelve Washes

| Attribute | % Who Preferred Untreated Towel | % Who Preferred Treated Towel | % Who Perceived No Difference in Samples |
|---|---|---|---|
| Lotionized | 21.0 | 41.0 | 38.0 |
| Softness | 21.0 | 38.0 | 41.0 |
| Smoothness | 23.0 | 44.0 | 33.0 |
| Silkiness | 21.0 | 42.0 | 37.0 |
| Moisturization | 21.0 | 38.0 | 41.0 |
| Overall | 28.0 | 46.0 | 26.0 |

Thus, as indicated from the representative examples above, a paper product of the present invention can provide numerous benefits to a user. It has been discovered that the particular selection and amount of ingredients utilized in the lotion of the present invention can provide a synergistic effect when applied to a paper product. For instance, the lotion applied to the paper product can help moisturize the skin of a user during use, as well as remaining on a user's hands for continued moisturizing affects. In some cases, the lotion can enhance the ability of a user's skin to retain water even after using the paper product. By retaining water, a user's skin can be prevented from becoming excessively dry, as well as being inhibited from developing certain skin problems, such as erythema. Moreover, the lotion can help to maintain the soft, smooth, and pliable appearance of the skin by its ability to remain on the skin surface, or in the stratum corneum to act as a lubricant, to reduce flaking, and to improve the skin's appearance. In some instances, the lotion can even help disinfect the skin of a user to inhibit the growth and/or spreading of various microbes.

In addition, as a result of the lower lotion add-on level that is obtainable in accordance with the present invention, a paper product formed therewith can also retain the ability to dry a person's skin. Thus, for example, a person can initially wash his/her hands using conventional soap. Thereafter, the person can utilize a paper product of the present invention for drying the wetted skin.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent paper product for drying and conditioning the skin of a user, wherein the paper product is in the form of a towel, wipe, or napkin, said paper product comprising:
   a paper web; and
   a water-soluble lotion composition applied to said paper web such that the add-on level of said lotion composition is between about 1% to about 10% by weight of said paper product, said lotion composition comprising:
   i) water in an amount between about 10% to about 90% by weight of said lotion composition;
   ii) a water-soluble skin conditioning component, said water-soluble skin conditioning component including glycerin in an amount between about 2% to about 15% by weight of said lotion composition; and
   iii) a viscosity-increasing component in an amount between about 2% to about 10% by weight of said lotion composition, said viscosity-increasing component including at least one alkoxylated alcohol surfactant.

2. A paper product as defined in claim 1, wherein said water comprises between about 10% to about 30% by weight of said lotion composition.

3. A paper product as defined in claim 1, wherein said water-soluble skin-conditioning component comprises between about 10% to about 40% by weight of said lotion composition.

4. A paper product as defined in claim 1, wherein said water-soluble skin-conditioning component further includes propylene glycol, sorbitol, or combinations thereof.

5. A paper product as defined in claim 1, wherein said water-soluble skin-conditioning component further includes sorbitol.

6. A paper product as defined in claim 5, wherein said sorbitol comprises between about 5% to about 20% by weight of said lotion composition.

7. A paper product as defined in claim 1, wherein said water-soluble skin-conditioning component further includes propylene glycol.

8. A paper product as defined in claim 7, wherein said propylene glycol comprises between about 5% to about 20% by weight of said lotion composition.

9. A paper product as defined in claim 1, wherein said viscosity-increasing component comprises between about 2% to about 5% by weight of said lotion composition.

10. A paper product as defined in claim 1, wherein said surfactant of said viscosity-increasing component includes PEG-80 glyceryl cocoate, behentrimonium methosulfate and cetearyl alcohol, PEG-2000, sodium stearoyl lactylate, PEG-75 lanolin, talloweth-60-myristyl glycol, or combinations thereof.

11. A paper product as defined in claim 1, further comprising a surfactant that inhibits the lotion composition from separating into more than one liquid phase, said surfactant comprising between about 20% to about 40% by weight of said lotion composition.

12. A paper product as defined in claim 1, wherein said lotion composition further comprises an antimicrobial agent.

13. A paper product as defined in claim 12, wherein said antimicrobial agent is present in an amount between about 0.01% to about 5% by weight of said lotion composition.

14. A paper product as defined in claim 1, wherein said lotion composition further comprises a preservative.

15. A paper product as defined in claim 14, wherein said preservative comprises between about 0.1% to about 2% by weight of said lotion composition.

16. A paper product as defined in claim 1, wherein said add-on level of said lotion is between about 1% to about 5% by weight of said paper product.

17. A paper product as defined in claim 1, wherein said paper product has a basis weight between about 1 to about 50 pounds per ream.

18. A paper product as defined in claim 1, wherein said paper product is a towel having a basis weight between about 10 to about 45 pounds per ream.

19. An absorbent paper towel for drying and conditioning the skin of a user, said towel having a basis weight from about 10 to about 45 pounds per ream, said towel comprising:
   a paper web; and
   a water-soluble lotion composition applied to said paper web such that the add-on level of said lotion is between about 1% to about 10% by weight of said paper towel, said water-soluble lotion composition comprising:
   i) water in an amount between about 10% to about 30% by weight of said lotion composition;
   ii) a water-soluble skin-conditioning component in an amount between about 10% to about 40% by weight of said lotion composition, wherein said water-soluble skin-conditioning component includes glycerin in an amount between about 2% to about 15% by weight of said lotion composition; and
   iii) a viscosity-increasing component in an amount between about 2% to about 5% by weight of said lotion composition, said viscosity-increasing component including at least one alkoxylated alcohol surfactant.

20. A paper towel as defined in claim 19, wherein said water-soluble skin-conditioning component further includes sorbitol in an amount between about 5% to about 20% by weight of said lotion composition.

21. A paper towel as defined in claim 19, wherein said water-soluble skin-conditioning component further includes propylene glycol in an amount between about 5% to about 20% by weight of said lotion composition.

22. A paper towel as defined in claim 19, wherein said lotion composition further comprises an antimicrobial agent.

23. A paper towel as defined in claim 19, wherein said lotion composition further comprises a preservative.

24. A paper towel as defined in claim 19, wherein said add-on level of said lotion is between about 1% to about 5% by weight of said paper product.

25. A paper product as defined in claim 1, wherein said surfactant of said viscosity-increasing component includes talloweth-60-myristyl glycol.

26. A paper towel as defined in claim 19, wherein said surfactant of said viscosity-increasing component includes talloweth-60-myristyl glycol.

* * * * *